United States Patent [19]

Herrmann et al.

[11] 4,208,526
[45] Jun. 17, 1980

[54] PROCESS FOR THE PREPARATION OF THIAZOLIDIN-4-ONE-ACETIC ACID DERIVATIVES

[75] Inventors: Wolfgang Herrmann, Merzhausen; Gerhard Satzinger, Denzlingen, both of Fed. Rep. of Germany

[73] Assignee: Warner-Lambert Company, Morris Plains, N.J.

[21] Appl. No.: 4,797

[22] Filed: Jan. 19, 1979

[30] Foreign Application Priority Data

Jan. 20, 1978 [DE] Fed. Rep. of Germany ....... 2802387

[51] Int. Cl.$^2$ ............................................. C07D 417/04
[52] U.S. Cl. ....................................................... 546/209
[58] Field of Search ......................................... 546/209

[56] References Cited

U.S. PATENT DOCUMENTS 3,072,653  1/1963  Satzinger ............................. 546/209
3,971,794  7/1976  Satzinger et al. ..................... 546/209

*Primary Examiner*—Henry R. Jiles
*Assistant Examiner*—Robert T. Bond
*Attorney, Agent, or Firm*—George M. Kaplan; Albert H. Graddis

[57] ABSTRACT

A new and chemically unique one-pot process for the preparation of thiazolidin-4-one-acetic acid derivatives of the general formula:

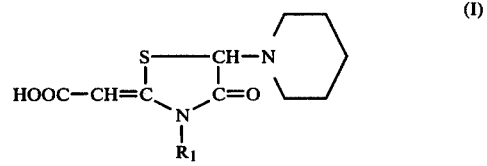

wherein $R_1$ is a lower alkyl radical.

7 Claims, No Drawings

PROCESS FOR THE PREPARATION OF THIAZOLIDIN-4-ONE-ACETIC ACID DERIVATIVES

SUMMARY

The present invention is concerned with a new and chemically unique one-pot process for the preparation of thiazolidin-4-one-acetic acid derivatives of the general formula:

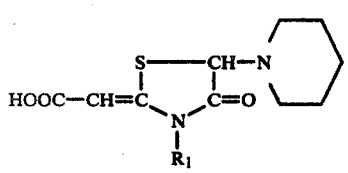

wherein $R_1$ is a lower alkyl radical.

In this new process, the 5-bromo derivatives of the corresponding carboxylic acid alkyl esters are prepared by reaction with elementary bromine in a solvent of low polarity. The hydrogen bromide thereby formed splits the ester bond at elevated temperatures, whereupon the 5-bromo derivatives of the free acid can be directly reacted in situ with piperidine.

The present invention is concerned with a chemically unique process for the preparation of thiazolidin-4-one-acetic acid derivatives.

2-Carbalkoxymethylene-3-alkyl-5-bromothiazolidin-4-one derivatives are known from German Patent Specification No. 1,160,441 and are prepared by the reaction of 2-carbalkoxymethylene-3-alkyl-thiazolidin-4-one derivatives with elementary bromine in an inert solvent.

These compounds are used as intermediates for the preparation of the known diuretically-active or choleretically-active pharmaceuticals etozolin and piprozolin (WHO names), as well as for the preparation of diuretically and choleretically-active compounds according to German Patent Specification No. 2,414,345.

When carrying out the conversion into compounds according to German Patent Specification No. 2,414,345, there is the difficulty of hydrolysing the carboxymethylene group without destroying the ring system, which is known to be labile. In this German Patent Specification No. 2,414,345, it was suggested to carry out the ester splitting with 40% hydrobromic acid, which had proved to be especially suitable for this purpose. According to the known process, the reaction could be carried out with a yield of about 55%.

We have now found that the free thiazolidine-acetic acid derivatives described in German Patent Specification No. 2,414,345 can be prepared in high yield by a surprisingly simple and elegant one-pot method when the steps of bromination, ester splitting and the introduction of the piperidino group are combined in a definite sequence and under special conditions.

Thus, according to the present invention, there is provided a process for the preparation of compounds of the general formula:

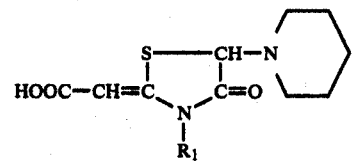

in which $R_1$ is an alkyl radical containing up to 3 carbon atoms, wherein a compound of the general formula:

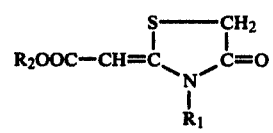

in which $R_1$ has the same meaning as above and $R_2$ is an alkyl radical containing 3 to 6 carbon atoms, is reacted in an inert solvent of low polarity with an at least equimolar amount of bromine and the compound thus obtained of the general formula:

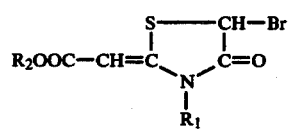

in which $R_1$ and $R_2$ have the same meanings as above, is subjected to an ester splitting in situ by the action of the hydrogen bromide present in the reaction mixture to give a compound of the general formula:

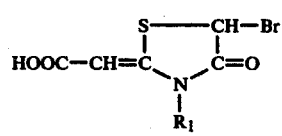

in which $R_1$ has the same meaning as above, which, without isolation, is reacted with at least an equivalent amount of piperidine.

Because of the hydrogen bromide formed, the reaction of the compounds (IV) with piperidine is, in fact, preferably carried out with a larger molar excess thereof and more preferably with a fivefold molar amount.

It is extremely surprising that the hydrogen bromide formed in the course of the bromination of the compounds (II) in a solvent of low polarity is able quantitatively to split the ester group although it was known that in acetic acid, which is highly polar and which is more suitable for such reactions, with excess 40% hydrogen bromide it was only possible to achieve yields of about 56%. Furthermore, it is surprising that the compounds of general formula (IV) are so stable that, in spite of the reaction which preferably takes place at an elevated temperature, it can be reacted with piperidine in a one-pot reaction practically without losses.

The process according to the present invention has the great advantage that the ester splitting, which otherwise has to be carried out in the last stage of the synthesis and can only be carried out with unsatisfactory yields, takes place at an earlier stage more or less as a side reaction. At the same time, the hydrogen bromide which previously had to be removed from the exhaust air in a wash tower is "internally" utilised in the one-pot process with the formation of alkyl bromides, which is a further advantage, especially from the point of view of a large scale preparation.

The process according to the present invention enables the desired thiazolidine-acetic acid derivatives of general formula (I) to be prepared in only two successive process steps with a total yield of about 80% of theory, in comparison with a yield of about 20% of theory according to the process of German Patent Specification No. 2,414,345. This means an increase in yield of the order of 300% with a much simpler carrying out of the process.

Compounds of general formula (II) which are preferably used are those in which $R_1$ is a methyl or ethyl radical and $R_2$ is a tert.-butyl radical.

As inert solvent, it is preferred to use a halogenated hydrocarbon, for example chloroform or dichloromethane.

The bromination is preferably carried out at a temperature of from $-25°$ C. to ambient temperature. The ester splitting can be accelerated by increasing the temperature to reflux temperature and is thus carried out in a relatively short period of time. However, the reaction can also be carried out at only a moderately increased temperature while putting up with a longer reaction time.

The subsequent reaction of the compounds (IV) with piperidine is preferably carried out in the cold and more preferably at a temperature of about $-15°$ C., the piperidine preferably being added in the form of a solution in the solvent which has been selected for the reaction.

The compounds (I) can be isolated in known manner by extraction with a base and preferably with a dilute aqueous solution of an alkali metal hydroxide and liberation of the free acid by means of an appropriate acid, for example acetic acid.

The following Examples are given for the purpose of illustrating the present invention:

EXAMPLE 1

(Z)-3-Methyl-4-oxo-5N-piperidino-thiazolidin-2-ylidene)acetic acid 114.6 g. (0.5 mole) tert.-Butyl (3-methyl-4-oxo-thiazolidin-2-ylidene)-acetate are dissolved in 1000 ml. chloroform in a 2 liter three-necked flask equipped with a stirrer, a cooler, an internal thermometer and a dropping funnel provided with an extended run-off tube. While cooling with a cooling bath having a temperature of $-25°$ C., 80.0 g. (0.5 mole) bromine in 220 ml. chloroform are allowed to run in below the surface within a period of 30 minutes at an internal temperature of $-15°$ C. The cooling bath is then removed and the temperature is increased to 20° C. within the course of 1 hour. The reaction mixture is subsequently boiled under reflux for 30 minutes, whereafter it is again cooled to $-15°$ C. and 212.8 g. (2.5 mole) piperidine in 250 ml. chloroform are added dropwise in the course of 30 minutes. Stirring is then carried out for 1 hour at ambient temperature, followed by extraction twice with 500 ml. amounts of 1 N aqueous sodium hydroxide solution and twice with 250 ml. amounts of 1 N aqueous sodium hydroxide solution. The combined alkaline extracts are acidified with 250 ml. acetic acid and the precipitated product is filtered off with suction. There are obtained 110 g. (92.6% of theory) (Z)-3-methyl-4-oxo-5N-piperidino-thiazolidin-2-ylidene)acetic acid; m.p. 165° C. (decomp.).

The tert.-butyl (3-methyl-4-oxo-thiazolidin-2-ylidene)acetate used as starting material is prepared in the following manner:

141.17 g. (1.00 mole) tert.-Butyl cyanoacetate and 120.17 g. (1.00 mole) ethyl thioglycolate are placed in a 2 liter three-necked flask equipped with a stirrer, cooler, dropping funnel and internal thermometer. 145.12 g. (1.05 mole) potassium carbonate are introduced at ambient temperature, with stirring. After a short period of time, an exothermal reaction commences and the contents of the flask solidify. The stirrer is switched off and the reaction mixture is left to stand without heating or cooling. The internal temperature thereby temporarily increases to about 60° C. After 1 hour, 1000 ml. acetone are added thereto and the substance is dissolved at 40° C. with careful stirring. Subsequently, the reaction mixture is cooled to 30° C. and 132.43 g. (1.05 mole) dimethyl sulphate are added dropwise in the course of 15 minutes and allowed to react for 2 hours at 40° C., while stirring.

Half of the acetone is subsequently evaporated off on a rotary evaporator at a water-bath temperature of 40° C. and the residue is mixed with 1000 ml. water. Further distillation is carried out until no more acetone passes over, whereupon the batch is cooled to ambient temperature and stirred until the initially oily product completely crystallises. It is filtered off with suction, then washed with 500 ml. water and dried at 40° to 50° C. There are obtained 212.4 g. (92.6% of theory) tert.-butyl (3-methyl-4-oxo-thiazolidin-2-ylidene)-acetate; m.p. 76.6° C. The product has a thin layer chromatographic purity of 98–99%.

EXAMPLE 2

(Z)-3-Ethyl-4-oxo-5N-piperidino-thiazolidin-2-ylidene)acetic acid 121.6 g. (0.5 mole) tert.-Butyl (3-ethyl-4-oxothiazolidin-2-ylidene)-acetate are dissolved in 1000 ml. chloroform in a 2 liter three-necked flask equipped with a mechanical stirrer, cooler, internal thermometer and dropping funnel with an extended run-off tube. While cooling in a cooling bath having a temperature of $-25°$ C., 80.0 g. (0.5 mole) bromine in 220 ml. chloroform are allowed to run in below the surface, with vigorous stirring and at an internal temperature of $-15°$ C. The cooling bath is then removed and the temperature allowed to increase to 20° C. in the course of 1 hour. The reaction mixture is then brought to the boil and boiled under reflux for 30 minutes. It is then again cooled to $-15°$ C. and 212.8 g. (2.5 mole) piperidine in 250 ml. chloroform are added dropwise thereto within the course of 30 minutes. The batch is then brought to ambient temperature, stirred for 1 hour and subsequently extracted twice with 500 ml. amounts of 1 N aqueous sodium hydroxide solution and twice with 250 ml. amounts of 1 N aqueous sodium hydroxide solution. The combined alkaline extracts are acidified with 250 ml. acetic acid and the precipitated product is filtered off with suction. The crystals thus obtained are then washed on the filter with 1000 ml. water and dried at 50° C. There are obtained 112 g. (82.9% of theory) (Z)-3-ethyl-4-oxo-5N-piperidino-thiazolidin-2-ylidene)-acetic acid which has a thin layer chromatographically determined purity of >99%.

The tert.-butyl (3-ethyl-4-oxo-thiazolidin-2-ylidene)-acetate used as starting material is prepared in the following manner:

141.17 g. (1.00 mole) tert.-Butyl cyanoacetate and 120.17 g. (1.00 mole) ethyl thioglycolate are placed in a 2 liter three-necked flask equipped with a mechanical stirrer, cooler, dropping funnel and internal thermometer and 145.12 g. (1.05 mole) potassium carbonate are introduced at ambient temperature, while stirring. After a short time, an exothermal reaction commences and the flask contents solidify. The stirrer is switched off and the reaction mixture is left to stand without heating or cooling. The internal temperature thereby temporarily increases to about 60° C. After 1 hour, 1000 ml. acetone and 154 ml. (2 mole) dimethyl formamide are added thereto and the solidified substance then dissolved at 30° C., while stirring carefully. Subsequently, 161.89 g. (1.05 mole) diethyl sulphate are added dropwise thereto within the course of 15 minutes, while stirring, and the reaction allowed to take place at 40° C. for a period of 3 hours. About half of the acetone is then distilled off on a rotary evaporator at a waterbath temperature of 40° C. and the residue is mixed with 1000 ml. water. The batch is further distilled until no more acetone passes over, then cooled to ambient temperature and stirred until the initially oily product has completely crystallised. The product is filtered off with suction, then washed with 1000 ml. water and dried at 40° to 50° C. There are obtained 218.3 g. (89.7% of theory) tert.-butyl (3-ethyl-4-oxo-thiazolidin-2-ylidene)-acetate; m.p. 72.7° C. The product has a thin layer chromatographic purity of about 97%.

What we claim is:

1. A process for the preparation of a thiazolidin-4-one-acetic acid of the formula:

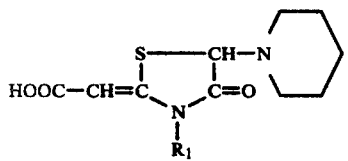

in which $R_1$ is an alkyl radical containing up to 3 carbon atoms, wherein a compound of the formula:

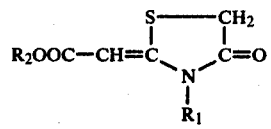

in which $R_1$ has the same meaning as above and $R_2$ is an alkyl radical containing 3 to 6 carbon atoms, is reacted at a low temperature in an inert solvent of low polarity with at least an equimolar amount of bromine and the compound thus obtained of the formula:

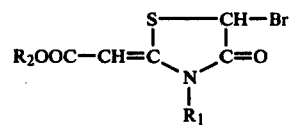

in which $R_1$ and $R_2$ have the same meanings as above, is subjected in situ to an ester-splitting by the action of the hydrogen bromide present in the reaction mixture and the compound thus obtained of the formula:

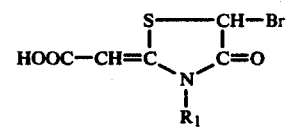

in which $R_1$ has the same meaning as above, is, without isolation, reacted with at least an equivalent amount of piperidine.

2. A process according to claim 1, wherein the inert solvent is a halogenated hydrocarbon.

3. A process according to claim 2, wherein the halogenated hydrocarbon is dichloromethane or chloroform.

4. A process according to any of the preceding claims, wherein the bromination is carried out at a temperature of from −25° C. to ambient temperature.

5. A process according to any of the preceding claims, wherein the ester splitting is accelerated by increasing the temperature to the reflux temperature of the solvent.

6. A process according to any of the preceding claims, wherein the reaction with piperidine is carried out in the cold.

7. A process according to claim 6, wherein the reaction with piperidine is carried out at a temperature of about −15° C.

* * * * *